United States Patent [19]
Porat et al.

[11] Patent Number: 4,719,915
[45] Date of Patent: Jan. 19, 1988

[54] SCALPEL

[76] Inventors: Michael Porat, 52 Hamitnadev St., Tel Aviv; Amir Porat, 22 Rachvat Eilan St., Givat Shaul, Ramat Eilan, both of Israel

[21] Appl. No.: 858,744

[22] Filed: May 2, 1986

[30] Foreign Application Priority Data

May 5, 1985 [IL] Israel .................................... 75096

[51] Int. Cl.⁴ ............................................ A61B 17/32
[52] U.S. Cl. ..................................... 128/305; 30/286; 30/295
[58] Field of Search ............... 128/305, 304, 346, 340, 128/751; 30/329, 339, 321, 286, 285, 295

[56] References Cited

U.S. PATENT DOCUMENTS

D. 242,179  11/1976  Sugiyama et al. ............... D83/12 R

FOREIGN PATENT DOCUMENTS

| 2058903 | 7/1974 | Fed. Rep. of Germany | 128/305 |
| 2487188 | 1/1982 | France | 128/305 |
| 2518394 | 6/1983 | France | 128/305 |
| 848,388 | 9/1960 | United Kingdom | 128/305 |

Primary Examiner—Michael H. Thaler
Attorney, Agent, or Firm—Dennison, Meserole, Pollack & Scheiner

[57] ABSTRACT

A holder for a surgical blade comprising a handle and a detachable blade shield integrally formed with said handle, the blade shield including a member defining a sleeve into which the blade can be inserted after detachment of the shield from the handle.

9 Claims, 6 Drawing Figures

SCALPEL

FIELD OF THE INVENTION

The present invention relates to a disposable holder for a surgical knife blade, in general, and to a holder including a detachable blade protector, in particular.

BACKGROUND OF THE INVENTION

Surgical knife blades mountable in holders for use have long been known. The holders were typically made of metal into which the knife blade was inserted before use and from which the knife blade was removed after use.

With the development of plastics, disposable plastic blade holders were developed with surgical knife blades mounted thereon, ready for use. However, in order to prevent inadvertent contact with the blade before use, some sort of protective cover was required. Cardboard or other tubing, for example, was provided to be placed about the blade during transportation and again for disposal.

There is shown in German Patentschrift No. 2 058 903 a blade holder including a snap-off protective shield integrally formed with the holder and arranged to be removed before use. This shield serves to protect persons handling the holder from contacting the blade before it is used, the shield being thrown away after being removed. Thus, it provides no protection for the used blade at the time of disposal, which can cut the disposal plastic bag or the user when discarded.

There is shown in U.K. Pat. No. 848,388 a cutting tool having a blade supported in a handle, and a sheath enclosing the cutting edge of the blade moulded onto the blade by insert molding and attached to the handle by a readily frangible connection therewith. The sheath is removed by rotating it about the blade and breaking the connection to the handle. There is no suggestion of using the sheath again after use of the cutting tool and, due to the nature of the insert molding process and the bond formed thereby, the sheath of this patent can not physically be replaced on the blade once it is removed.

SUMMARY OF THE INVENTION

It is accordingly an object of the present invention to provide a holder for a surgical blade including an integrally formed blade shield which can also be used to cover the blade upon disposal.

There is thus provided in accordance with the present invention a holder for a surgical blade including a handle and a selectably removable blade shield, integrally formed with the handle, the blade shield including a member defining a sleeve into which the blade can be inserted after the shield is detached from the handle.

According to a preferred embodiment of the invention, the member defines a cross section of gradually increasing thickness for frictional engagement of the blade.

Further according to a preferred embodiment, the member includes a cross bar defining a bridge element. Preferably, the inlet of the bridge element is larger than the outlet of the bridge element for increased engagement of the blade.

Still further according to a preferred embodiment, the holder also includes a surgical knife blade affixed thereto.

BRIEF DESCRIPTION OF THE DRAWINGS

The apparatus of the present invention will be further understood and appreciated from the following detailed description taken in conjunction with the drawings in which.

DETAILED DESCRIPTION OF THE INVENTION

Figure 1:
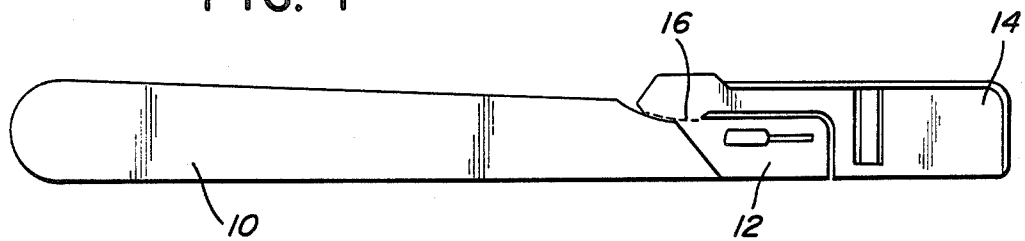
FIG. 1 is a plan view of a holder for a surgical blade constructed and operative in accordance with an embodiment of the present invention.

With reference to FIG. 1 there is shown a holder for a surgical blade constructed and operative in accordance with an embodiment of the present invention and including a handle 10, blade attachment member 12, and blade shield 14. Handle 10 and blade attachment member 12 may be of any conventional construction or shape and may be formed of any conventional material, preferably plastic. Blade shield 14, which may be of any desired shape or material, is integrally formed with handle 10 and is selectably removable or detachable therefrom by bending and breaking the connection between them, as indicated by the broken lines 16.

Figure 2B:
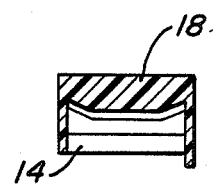
FIG. 2B is a sectional view taken along line A—A of FIG. 2A.
Figure 2A:
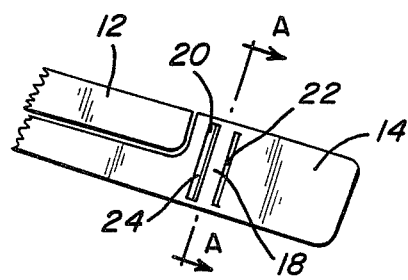
FIG. 2A is a perspective view of the bridge portion of the holder of FIG. 1.

With additional reference to FIG. 2A, it can be seen that blade shield 14 includes an elevated bridge member comprising a cross bar 18. A sleeve 20 is defined by bridge member 18 and shield 14 into which the used surgical blade can be inserted for disposal. Alternatively, any other form of sleeve or pocket member may be provided in blade shield 14 to accomodate the surgical blade.

According to a preferred embodiment of the invention, the sleeve defined in shield 14 is tapered and gradually narrows from the inlet aperture. Thus, for example, as shown in FIG. 2B, the cross bar of bridge member 18 is tapered from the forward edge, or outlet, 22 of sleeve 20 towards the rear edge, or inlet, 24 of sleeve 20. Thus, inlet 24 is higher than outlet 22, which is preferably rectangular to press more efficiently on the blade. It is a particular feature of this embodiment that increased frictional engagement of the blade by the sleeve defining member is provided to prevent slippage of the shield from the blade.

Figure 3:
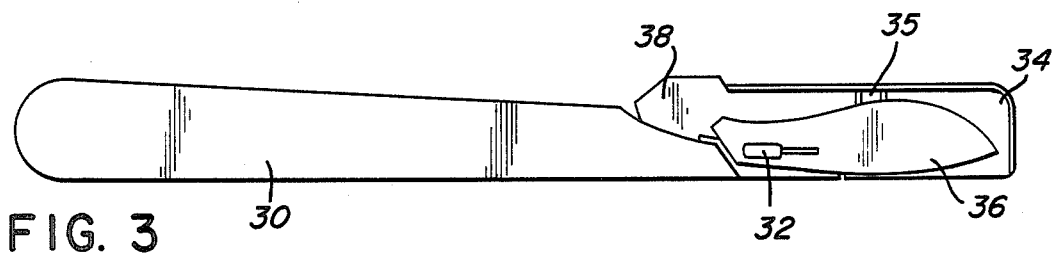
FIG. 3 is a plan view of a holder of the present invention with a surgical knife blade affixed thereto.
Figure 4:
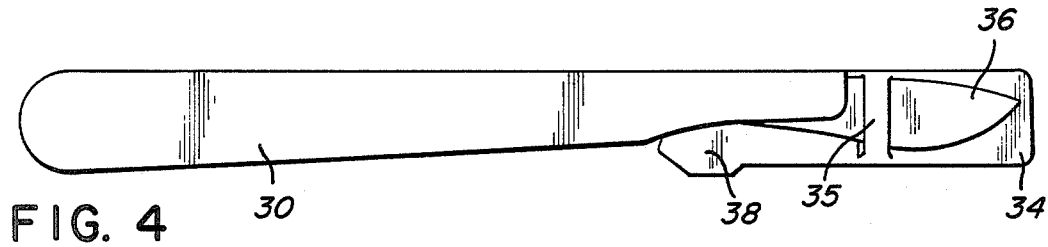
FIG. 4 is a bottom view of the holder of FIG. 3 after use and ready for disposal.

Operation of the holder of the present invention can be seen more clearly in FIGS. 3 and 4. In FIG. 3, there is shown a holder including a handle 30, blade attachment means 32 and blade shield 34 including a bridge member 35. A surgical blade 36 is affixed to the holder about blade attachment means 32, preferably during production of the holder. As can be seen, blade shield 34 extends beyond the edges of surgical blade 36 preventing inadvertent contact with the blade itself.

When it is desired to use the surgical blade, blade shield 34 is removed by pressing on release tab 38, snapping the blade shield from the remainder of the handle.

It is clear that the blade should remain affixed to handle 30.

After use of the blade, when it is desired to dispose of the holder and blade, surgical blade 36 is mounted in blade shield 34 by inserting it into the sleeve formed by bridge member 36. As can be seen in FIG. 4, blade shield 34 again extends beyond the edges of the blade, preventing inadvertent contact therewith.

Figure 5:
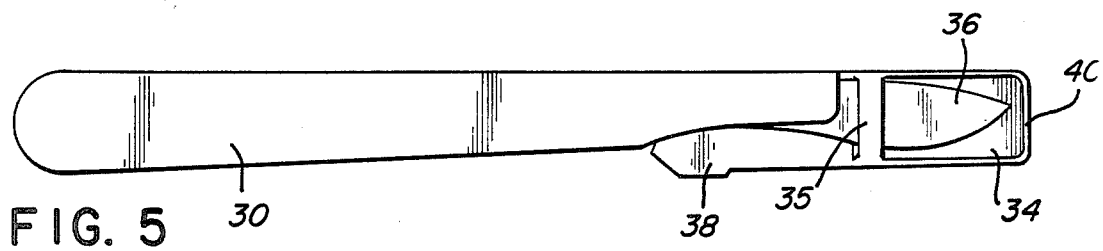
FIG. 5 is a bottom view of a surgical blade holder constructed and operative in accordance with an alternate embodiment of the invention.

With reference to FIG. 5 there is shown a blade holder substantially as illustrated in FIGS. 3 and 4, like portions being indicated by like reference numerals. The blade holder of this embodiment further defines a peripheral flange 40 or perpendicular wall about the periphery on the bottom of blade shield 34. The addition of this flange confines the blade within the shield, preventing inadvertent contact therewith in the event that it swivels within the bridge member or during insertion.

It will be appreciated that, while the blade holder has been illustrated with reference to a surgical blade of a particular shape, the blade holder can be adapted to protect a surgical blade of any known size and shape.

It will further be appreciated by those skilled in the art that the present invention is not limited to what has been shown and described hereinabove by way of example. Rather, the scope of the invention is limited solely by the claims which follow.

We claim:

1. A surgical instrument including a handle, a surgical blade mounted on said handle with a portion of the blade projecting from said handle, a blade shield extending from said handle, said blade shield underlying said blade and extending peripherally beyond the projecting portion of said blade, and frangible means integrally joining said shield with said handle for a selective manual breaking of said shield from said handle for an exposure of the projecting portion of said blade, said blade shield including sleeve means receivable over the projecting portion of said blade after detachment of the shield from the handle for a selective retention of the shield on said blade with said shield projecting peripherally beyond the projecting portion of said blade, said sleeve means including means for frictionally engaging and retaining said blade therein, said blade, prior to detachment of the shield from the handle, being external of said sleeve means, said shield being generally planar with first and second opposed generally parallel surfaces, said first surface being generally planar and immediately underlying said blade prior to detachment of said shield from said handle, said sleeve means being on said second surface remote from said blade prior to detachment of said shield whereby detachment and repositioning of said shield is required prior to reception of said blade in sleeve means.

2. A surgical instrument according to claim 1 and wherein said sleeve means is tapered to define the means for frictional engagement and retention of said blade.

3. A surgical instrument according to claim 2 and wherein said sleeve means is defined by a bridge member comprising a cross bar.

4. A surgical instrument according to claim 3 and wherein said cross bar is tapered for frictional engagement of said blade.

5. A surgical instrument according to claim 1 and wherein said sleeve means is defined by a bridge member comprising a cross bar.

6. A surgical instrument according to claim 5 and wherein said cross bar is tapered for frictional engagement of said blade.

7. A surgical instrument according to claim 1 and wherein said shield defines a pocket for accomodating said blade after detaching.

8. An instrument as in any of claims 1, 2, 5, 3, 6, 4 or 7 and further defining a peripheral flange about said blade shield on the same surface as the sleeve means.

9. A surgical instrument as claimed in claim 1 and wherein said sleeve means is adapted to protect said blade.

* * * * *